United States Patent [19]

Hunt

[11] 4,179,398

[45] Dec. 18, 1979

[54] PLATELET CONTROL COMPOSITION

[75] Inventor: Roger A. Hunt, Woodland, Wash.

[73] Assignee: ICN Medical Laboratories, Inc., Portland, Oreg.

[21] Appl. No.: 779,322

[22] Filed: Mar. 21, 1977
(Under 37 CFR 1.47)

[51] Int. Cl.$^2$ .................. G01N 33/16; C09K 3/00
[52] U.S. Cl. .................. 252/408; 23/230 B; 356/39; 356/42; 424/2; 424/3; 424/95
[58] Field of Search .................. 252/408; 23/230 B; 424/2, 3, 95; 356/39, 42

[56] References Cited

U.S. PATENT DOCUMENTS

| | | | |
|---|---|---|---|
| 3,406,121 | 10/1968 | Jones | 252/408 |
| 3,519,572 | 7/1970 | Kita | 252/408 |
| 3,558,522 | 1/1971 | Louderback et al. | 252/408 |
| 3,574,137 | 4/1971 | De Casperis | 252/408 |
| 3,632,735 | 1/1972 | Kita | 424/3 |
| 3,640,896 | 2/1972 | De Casperis | 252/408 |
| 3,705,110 | 12/1972 | Louderback et al. | 252/408 |
| 3,873,467 | 3/1975 | Hunt | 252/408 |
| 3,962,125 | 6/1976 | Armstrong | 252/408 |
| 3,973,913 | 9/1976 | Louderback | 23/230 B |
| 3,977,995 | 8/1976 | Louderback et al. | 252/408 |

OTHER PUBLICATIONS

C. A., vol. 84, 103068s (Jan.–Jun. 1976), Citing Lewis, J. H., Excerpta Med. Int. Congr. Ser., No. 357, pp. 18–23 (1975).

C. A., vol. 80, 1824k (1974), Citing Kahn, R. A., et al., Amer. J. Physiol., vol. 225, No. 4, pp. 770–775 (1973).

*Primary Examiner*—Benjamin R. Padgett
*Assistant Examiner*—T. S. Gron
*Attorney, Agent, or Firm*—Chernoff & Vilhauer

[57] ABSTRACT

A platelet reference control composition comprising goat blood cells shrunken to the size of human platelets.

5 Claims, No Drawings

PLATELET CONTROL COMPOSITION

BACKGROUND OF THE INVENTION

1. Field of the Invention

This invention relates to a hematologic reference control. It relates particularly to a composition which can be used as a reference standard in making hematologic determinations. Most particularly, it relates to a novel composition which may be used as a reference in calculating platelet counts in human blood and in calibrating automated and manual devices designed to measure such, such as electronic counters and bright field microscopes or the Phase Microscope.

2. State of the Art

With the advent of improved automated devices for hematological study in the past decade, there has arisen a need for stable reference controls. In response to this need, a number of stabilized controls and methods of producing such have been developed. See, for example, all of the following U.S. Patents which pertain to controls for red and white blood cell counts: U.S. Pat. Nos. 3,873,467, 3,640,896, 3,632,735 and 3,754,137. The former two patents relate to stabilized compositions of human blood cells, while the latter two relate to stabilized compositions of mixtures of blood from humans and fowl. See also U.S. Pat. No. 3,558,522, wherein is disclosed a fluid suspension containing red blood cells and synthetic latex particles which is also useful as a control for red and white blood cell counts.

Although there are a number of platelet reference controls currently on the market, they are composed of human platelets, and so suffer from a variety of drawbacks. Platelets play a key role in coagulation of human blood by disintegrating when blood escapes from the blood vessels and liberating thromboplastins which convert prothrombin to thrombin, which in turn causes clotting. Consequently, human platelets are naturally unstable outside an environment of human blood. Principal problems presented by the use of human platelets as a reference control are the tendency of the platelets to disintegrate or lyse prematurely (hemolysis), thus giving such compositions a relatively short shelf-life, and undue agglutination and agglomeration.[1] Because of this, a primary problem of the prior art has been in achieving stablized compositions with sufficient shelf-life to be of practical use. Even stabilized compositions of human platelets are subject to problems such as the need for preservation at or below a critical temperature by refrigeration, undesirable electrolytic effects which tend to interfere with the accuracy of electronic counters, the tendency toward undue cell association, and non-uniformity in suspension. Other common problems in the art are obtaining submicroscopic particulates with a sufficiently narrow range of mean volumes, with sufficient uniformity of shape, and with appropriate electroconductivity to be useful as reference controls.

[1] Hereinafter the problems of agglutination and agglomeration will be collectively referred to as "cell association."

SUMMARY OF THE INVENTION

It is a primary object of the present invention to provide a new and improved control standard for use in human blood platelet counts.

Another object of this invention is to provide a stable hematological control standard for calibrating automatic and manual platelet counting devices.

A further object is to provide a platelet reference control standard which is extremely stable, needs no refrigeration, has no undesirable electrolytic effects, has a narrow range of mean cell volumes, has uniformly sized particulates, has good electroconductivity, and is virtually free from cell association and hemolysis.

These and other objects as well as the manner of achieving them will become apparent to those skilled in the art from the detailed description which follows.

According to the present invention, a stable platelet reference control standard is provided by a composition comprising a fluid suspension of red blood cells of a goat shrunken to substantially the size of human blood platelets.

DESCRIPTION OF PREFERRED EMBODIMENTS

The essence of the present invention lies in the discovery that red blood cells of a goat contain suitable characteristics to allow them to be shrunken without excessive cell association and hemolysis to approximate the size of human blood cell platelets with a narrow range of mean cell volumes and in spherical shape.

The novel composition of this invention is produced essentially by a simple, three-step procedure comprising (1) preferentially precipitating red blood cells from whole goat blood, (2) shrinking the red blood cells, and (3) fixing the shrunken cells.

Starting Material

The starting material for the composition of the present invention may be whole goat blood of any of the common species of goat. There is no concern about any specific antigen or group of antigens, such as the hepatitis-associated antigens that are occasionally present in human platelet compositions, so no precautions therefor are necessary. Goat red blood cells normally are about 4.1 microns in diameter and have a volume of about 35 cubic microns.

Precipitation Step

The red blood cells of goat blood are preferentially precipitated, that is, caused to settle out at a faster rate than the remainder of the blood cell components, by mixing the blood with a solution comprising a polymerized sugar, a salt of a dicarboxylic acid, and a weak base.

Preferably the polymerized sugar is polymerized anhydroglucose, or, as it is commonly known in the art, Dextran, with a molecular weight of from about 100,000 to about 500,000. Most preferably, the Dextran should have a molecular weight of from about 150,000 to about 200,000. Another preferred polymerized sugar is polymerized sucrose of 500,000 molecular weight. The concentration of the polymerized sugar should be from about 20 to about 50 grams per liter, and most preferably about 30 grams per liter.

The salt of a dicarboxylic acid may be any of the common salts such as the alkali metal salts, while the dicarboxylic acid may be any such acid which is effective in assisting precipitation of the red blood cells. Preferably, the acid is oxalic acid or tartaric acid. The di-alkali metal salt of tartaric acid is most preferred since it tends to impart a spherical shape to the cells.

The weak base may be any common weak base such as ammonia, mono- or di-basic alkali metal phosphates or bicarbonates. Preferably, the weak base is sodium bicarbonate.

The salt of the dicarboxylic acid and the weak base should be in sufficient concentrations to impart to the precipitating solution a pH range of from about 6.0 to about 8.5, most preferably from about 6.5 to about 7.5. It has been discovered that the precipitation step is inversely pH dependent; that is, the lower the pH, the greater the precipitation rate.

It should be understood that there are many variations possible in the types and concentrations of the components of the precipitating solution set forth above which will suggest themselves to one of ordinary skill in the art, the only limitations being those of preventing undue red blood cell association and hemolysis.

Shrinking Step

The red blood cells precipitated in the precipitation step are drawn off and shrunk by suspending them in a series of aqueous hypertonic salt solutions. Since the principle of a cell shrinking in a hypertonic solution, or one in which the concentration of solutes is greater than the concentration of solutes in the cell, is a simple one, it is envisioned that any salt will do as the solute in this step of the invention, so long as it does not cause undue hemolysis or cell association. Addition of a reagent that has a dispersing effect is desirable, since it helps to prevent undue cell association. Suitable dispersing agents are the di-alkali metal salts of the naphthol-disulfonic acids, and the low molecular weight (less than 42,000) dextrans. The artisan will also recognize some potential limitations as to choice of salt if the composition of the invention is to be used in electrical platelet counters, giving due regard to the relative conductivity/resistance of the liquid suspension and any possible adverse electrolytic effects.

An especially suitable class of salts for the shrinking step because of their dual role as a dispersing agent and a shrinking agent are the di-alkali metal salts of the naphthol-disulfonic acids, such as the dipotassium salt of 2-Naphthol-6,8 disulfonic acid and the disodium salt of 2-Naphthol-3,6 disulfonic acid.

The precipitated red goat blood cells are shrunken by successively suspending them in aqueous solutions of the salt in successively increasing concentrations until the desired size range is achieved. Since human blood cell platelets are in the range of from about 1.8 to about 3.6 microns in diameter and have a volume from about 5 to about 25 cubic microns, this is the desired range of sizes. The normal platelet count in humans is from about 200,000 to about 400,000 per cubic millimeter, while low counts are as little as 75,000 per cubic millimeter. Thus, the desired cell population or density is from about 75,000 to about 400,000 cells per cubic millimeter. At all times it is important to maintain the concentration of the salt solution equal to or greater than the concentration of the next preceding solution so as to maintain hypertonicity and prevent any swelling of the cells.

The effective final concentration of the salt of the hypertonic solution should be in the range of from about 650 to about 700 milliequivalents, preferably about 680, per liter. This may be achieved in any number of additions of incremental concentrations, the only limitations being the practical ones of time and keeping the salt in solution without precipitation. In connection with the latter problem, it has been found especially useful to use equal portions of the dipotassium and disodium salts of naptholdisulfonic acids.

In a preferred embodiment of the invention the cells are successively suspended in three aqueous hypertonic solutions of successively greater concentrations, the first one ranging in concentration from about 100 to about 300 milliequivalents per liter, preferably 200 milliequivalents per liter, the second one being double the concentration of the first one, and the third being double the concentration of the second. By adding three volumes of the hypertonic solution each time to the remaining preceding suspension, the effective final concentration is in the preferred range. After each suspension, the cells will precipitate and the supernatant should be discarded. The shrinking process may be accelerated considerably by centrifugation after each suspension. A suitable range of speeds and times for centrifugation is from 1,000 to 3,000×g for about 10–20, preferably 15 minutes for each step. When the cells have shrunken to the desired size, they should be resuspended in a fresh solution of the same concentration as the last shrinking solution, in preparation for the fixing step.

Fixing Step

Fixing of the shrunken cells is important to toughen the cell membranes and to prevent biodegradation of the same. This is accomplished by contacting the suspension of the cells with a solution of an organic aldehyde such as formaldehyde or glutaraldehyde. The aldehyde may be added in concentrations anywhere from about 5% to about 50% by weight, so long as the final concentration thereof is in the range of from about 0.5% to about 1.0%, preferably about 0.6% by weight. As is the case with the precipitating and shrinking solutions, the only practical limitations on selection of an appropriate aldehyde and concentration thereof are elimination of undue cell association and hemolysis and potential undesirable electrolytic effects.

In a preferred embodiment, glutaraldehyde in concentrations below 50% by weight is dripped slowly into the hypertonic suspension of cells while the same is rapidly stirred. Since the addition of the fixing solution dilutes the hypertonic suspension, sufficient amounts of the hypertonic shrinking solution should be added to maintain the concentration thereof at the same level and so maintain the size of the shrunken cells.

The fixed cells are thereafter allowed to settle out, separated, washed with a buffered solution, and placed in a storage solution.

As an optional step prior to recovering the shrunken cells, in order to assure a high-quality product containing only the hardiest cells with a stabilized cell population, the cell suspension may be subjected to severe agitation by any appropriate means, such as sonic agitation. This step tends to destroy the weaker-membraned cells and thus leave the more hardy for use as a platelet-counting reference control.

The buffered washing solution should be neutral to alkaline, preferably in the pH range of from about 7.0 to about 10.0. Although any buffered solution may be used, with due regard to the problems of hemolysis, cell association and electrolytic effects noted above, a preferred set of buffering reagents includes sodium hydroxide, sodium bicarbonate, and sodium chloride. The shrunken cells should be washed with the buffered solution as many times as is necessary to obtain a clear supernatant, preferably at least three times.

The storage solution in which the cells are suspended may be virtually any fluid, including mere water, which does not have a deleterious effect on the fixed cells, such as causing hemolysis, cell association or biodegradation. A preferred storage solution is basically the same buffered solution used in the washing step with the addition of a bacteriocidal or bacteriostatic agent to prevent contamination and a dispersing agent. The bacteriocidal or bacteriostatic agent can be any known agent added in sufficient concentration to reduce or check bacterial growth. An inexpensive and preferred bacteriocidal/bacteriostatic agent is merthiolate. Another is the hydrochloride salt of tetracycline. Each may be added in a concentration of about 0.1 grams per liter. The dispersing agent may be gelatin, the dialkali metal salts of the naphthol-sulfonic acids, or a low molecular weight dextran. A preferred dispersing agent is dextran with a molecular weight of about 20,000 to about 41,000, preferably about 40,000, added in a concentration of about 30 grams per liter. If gelatin is used as the dispersing agent, a preferred concentration is 1%, while if a di-alkali metal salt of a naphthol-sulfonic acid is used, such as the dipotassium salt of 2-Naphthol 6,8-disulfonic acid, the preferred concentration is from about 0.02 to about 0.05, preferably about 0.04 molar.

If the platelet reference control is to be used in connection with electronic platelet counting devices, it preferably has an electrolyte in the storage fluid in order to facilitate electrical conductivity. However, the pH of the solution in such applications should be substantially neutral to alkaline and a buffering system which may double as an electrolyte is advantageously used to maintain the pH of the solution.

The cell population or density may be adjusted by any known dilution or concentration technique. For example, if the product shows a density of 300,000 cells per cubic millimeter, and the desired density is about 75,000, the fluid suspension should be diluted by adding three volumes of diluent to obtain the desired density.

In executing all of the above steps in order to assure high purity of product, it is preferable to use reagent grade chemicals, as opposed to technical grade. It is also preferable to take precautions against the cells sticking to glassware, which they have a natural tendency to do. A standard measure to accomplish this is to "silanize" all glassware to be used by coating it with a solution of tetramethyl silane in benzene, and subjecting the coating glassware to 100° C. (dry air) for 15 to 30 minutes.

EXAMPLES

Example 1

The solutions indicated in Table I were prepared in the amounts indicated, vacuum filtered through #50 filter paper, and allowed to come to room temperature.

One pint of whole goat blood at room temperature was mixed with three pints of solution A in a separatory funnel and allowed to stand for two days. The precipitated red blood cells were drawn off slowly, leaving a layer of red blood cells to be discarded with the supernatant to get rid of most of the precipitated white blood cells.

The precipitated red blood cells were then resuspended in three times their volume of solution B in the separatory funnel and allowed to precipitate for 72 hours, drained, and the supernatant discarded. The same procedure was repeated with solutions C and D for periods of 72 hours each.

Table I

| Compound | A | B | C | D | E | F |
|---|---|---|---|---|---|---|
| K Na tartrate | 150 meq/L | | | | | |
| Dextran 200,000 | 30 g/L | | | | | |
| $Na_2NSA^1$ | | 100 meq/L | 400 meq/L | 800 meq/L | | |
| $K_2NSA^2$ | | 100 meq/L | 400 meq/L | 800 meq/L | | |
| $NaHCO_3$ | 30 meq/L | | | | 1 g/L | 1 g/L |
| 1.0 molar NaOH | | | | | 15 ml/L | 15 ml/L |
| Merthiolate | | | | | | 0.1 g/L |
| Dextran 40,000 | | | | | | 30 g/L |
| NaCl | | | | | 8 g/L | 8 g/L |
| Amount in liters | 1 | 1 | 1 | 2 | 4 | 4 |

[1] Disodium salt of 2-Naphthol 3,6 disulfonic acid.
[2] Dipotassium salt of 2-Naphthol 6,8 disulfonic acid.

The fixation step was commenced by resuspending the cells in six times their volume of solution B in a polyethylene beaker on a magnetic stir plate. While the suspension was rapidly stirred, 50 ml of a purified 25% solution of glutaraldehyde was slowly dripped into the suspension. 400 meq/l each of $Na_2NSA$ and $K_2NSA$ was added to the suspension to maintain maximum hypertonicity, and allowed to rapidly stir for two hours. While the rapid stir continued, the suspension was sonicated at full power with a regular tip for 20 minutes.

Thereafter the cells were permitted to settle out at room temperature for two days, the suspension aspirated, and the supernatant discarded.

The cells were then resuspended in three times their volume of solution E and allowed to settle out and the supernatant discarded. The same procedure was repeated four times until the supernatant was clear.

The cells were then resuspended in three times their volume of solution F, poured into a tall clear vessel, allowed to settle out, withdrawn, and resuspended in solution F, and adjusted to a concentration of 10% by weight.

Upon microscopic examination, the cells were seen to have a range of mean diameters of 2.5-3.0 microns, mean cell volume of 12 cubic microns, and a density of 300,000 per cubic millimeter and was shown to have a shelf-life in excess of six months, stored at room temperature.

Examples 2-7

Example 1 was repeated with the variations of solution A shown in grams per liter in Table II with substantially the same results.

Table II

| | Example No. | | | | | |
|---|---|---|---|---|---|---|
| Compound | 2 | 3 | 4 | 5 | 6 | 7 |
| K Na tartrate | 2 | 2 | 2 | 2 | 2 | 2 |
| Dextran 200,000 to 300,000 | 30 | 30 | 30 | 30 | 30 | 30 |
| $NaHCO_3$ | 20 | 25 | 30 | 35 | 40 | 45 |

As mentioned above, it will be apparent to those skilled in the art that the suspension fluid in which the shrunken cells are used will vary widely according to the particular need. For example, for use in manual counting procedures utilizing bright field microscopy (400× total magnification) and high-powered microscopes, the suspension fluid may be nothing more than water. Many electronic platelet counters on the market differentiate platelets by differences in electrical conductivity, utilizing an electrolytic solution of known value as the machine reference. As the electrolytes vary in machines of different manufacturers, so, too, may the suspension fluid of the present invention, depending on the particular application.

The nature, scope, utility, and effectiveness of the present invention have been described and specifically exemplified in the foregoing specification. The terms and expressions which have been employed in the foregoing abstract and specification are used therein as terms of description and not of limitation, and there is no intention, in the use of such terms and expressions, of excluding equivalents of the features shown and described on portions thereof, it being recognized that the scope of the invention is defined and limited only by the claims which follow.

What is claimed is:

1. A fluid suspension comprising red blood cells of a goat shrunken to substantially the size of human blood platelets, and fixed, the fluid being such that it does not cause hemolysis, cell association or biodegradation of the fixed cells.

2. The composition of claim 1 wherein the cells are shrunken to a diameter ranging from about 1.8 to about 3.6 microns and to a volume ranging from about 5 to about 25 cubic microns and are present in a density from about 75,000 to about 400,000 cells per cubic millimeter.

3. The composition of claim 1 where the cells have been shrunken by suspension in an aqueous hypertonic solution and have been fixed in an aldehyde-containing solution.

4. The composition of claim 3 wherein the solute of the hypertonic solution is selected from the group consisting essentially of alkali metal salts of naphthol-sulfonic acids and the aldehyde is glutaraldehyde.

5. The composition of claim 1 wherein the suspension is substantially neutral to alkaline.

* * * * *